United States Patent
Hess

(10) Patent No.: US 10,188,725 B2
(45) Date of Patent: Jan. 29, 2019

(54) HYBRID CORE FELINE VACCINES

(71) Applicant: Elanco US Inc., Indianapolis, IN (US)

(72) Inventor: Jennifer Christine Hess, Ft. Dodge, IA (US)

(73) Assignee: Elanco US Inc., Greenfield, IN (US)

( * ) Notice: Subject to any disclaimer, the term of this patent is extended or adjusted under 35 U.S.C. 154(b) by 21 days.

(21) Appl. No.: 15/375,398

(22) Filed: Dec. 12, 2016

(65) Prior Publication Data

US 2017/0165356 A1 Jun. 15, 2017

Related U.S. Application Data

(60) Provisional application No. 62/267,005, filed on Dec. 14, 2015.

(51) Int. Cl.
| | |
|---|---|
| *A61K 39/12* | (2006.01) |
| *A61K 39/265* | (2006.01) |
| *A61K 39/23* | (2006.01) |
| *A61K 39/00* | (2006.01) |

(52) U.S. Cl.
CPC ............ *A61K 39/265* (2013.01); *A61K 39/12* (2013.01); *A61K 39/23* (2013.01); *A61K 2039/525* (2013.01); *A61K 2039/5252* (2013.01); *A61K 2039/5254* (2013.01); *A61K 2039/552* (2013.01); *A61K 2039/70* (2013.01); *C12N 2710/16734* (2013.01); *C12N 2750/14034* (2013.01); *C12N 2770/16034* (2013.01)

(58) Field of Classification Search
None
See application file for complete search history.

(56) References Cited

U.S. PATENT DOCUMENTS

| | | | |
|---|---|---|---|
| 3,892,627 | A | 7/1975 | Simons et al. |
| 3,944,469 | A | 3/1976 | Bittle et al. |
| 4,031,204 | A | 6/1977 | Davis |
| 4,287,178 | A | 9/1981 | Bittle |
| 4,522,810 | A | 6/1985 | Pedersen |
| 4,699,785 | A | 10/1987 | Pedersen |
| 4,708,871 | A | 11/1987 | Geysen |
| 4,791,062 | A | 12/1988 | Wiesehahn et al. |
| 5,374,424 | A | 12/1994 | Kelsey et al. |
| 6,010,703 | A | 1/2000 | Maes et al. |
| 6,231,863 | B1 | 5/2001 | Colau et al. |
| 6,355,246 | B1 | 3/2002 | Kruger et al. |
| 7,264,816 | B2 | 9/2007 | Foley et al. |
| 7,306,807 | B2 | 12/2007 | Huang et al. |
| 7,309,495 | B2 | 12/2007 | Foley et al. |
| 7,482,150 | B2 | 1/2009 | Foley et al. |
| 8,685,412 | B2 | 4/2014 | Huang et al. |
| 2006/0057159 | A1 | 3/2006 | Wyeth |

FOREIGN PATENT DOCUMENTS

| | | |
|---|---|---|
| EP | 0676467 A2 | 10/1995 |
| EP | 0732340 A2 | 9/1996 |
| EP | 0835930 A1 | 4/1998 |
| EP | 1018557 A2 | 7/2000 |
| WO | 1992/021375 A1 | 12/1992 |
| WO | 1993/001284 A1 | 1/1993 |
| WO | 1993/003760 A1 | 3/1993 |
| WO | 1993/006211 A1 | 4/1993 |
| WO | 1993/007898 A1 | 4/1993 |
| WO | 1996/036356 A1 | 11/1996 |
| WO | 1998/018933 A1 | 5/1998 |
| WO | 2003/062407 A1 | 7/2003 |
| WO | 2005/080416 A1 | 9/2005 |

OTHER PUBLICATIONS

Wilson et al. Co-administration of an adjuvanted FeLV vaccine together with a multivalent feline vaccine to cats is protective against virulent challenge with feline leukaemia virus, calicivirus, herpesvirus and panleukopenia virus.Trials in Vaccinology 3 (2014) 26-32.*
Day et al. A kinetic study of histopathological changes in the subcutis of cats injected with non-adjuvanted and adjuvanted multi-component vaccines. Vaccine 25 (2007) 4073-4084.*
Gupta et al. Vaccination of Cats with Attenuated Feline Immuno-deficiency Virus Proviral DNA Vaccine Expressing Gamma Inter-feron. J. Virol. 2007; 81(2): 465-473.*
Schenk et al. 2013 AAFP Feline Vaccination Advisory Panel Report, Journal of Feline Medicine and Surgery (2013) 15, 785-808.*
Freshney, R. I. (Ed.). (1986). *Animal cell culture: a practical approach* (vol. 8). Oxford:: IRL press.
Schmidt, J. J. (1986). DNA cloning: a practical approach vols. 1 and 2: Edited by DM Glover. pp. 190 and 245. IRL Press, Oxford. 1985 *Biochemical Education*, 14(2), 91-91.
Morris, G. E. (1996). Epitope Mapping Protocols in Methods in Molecular Biology, (vol. 66). Humana Press.
Weir, D. M. and Blackwell, C. C. (1986) Handbook of Experimental Immunology. (vols. I-IV). Blackwell Scientific Publications.
Woodward, J.(1986) Immobilised cells and enzymes (a practical approach), IRL Press, Oxford.
Hames, B. D., & Higgins, S. J. (Eds.). (1985). Nucleic acid hybridisation: a practical approach.
Gait, M. J. (1984). An introduction to modern methods of DNA synthesis. *Oligonucleotide Synthesis: A practical approach.*
Perbal, B. (1988). A practical guide to molecular cloning.

(Continued)

*Primary Examiner* — Janet L Andres
*Assistant Examiner* — Stuart W Snyder
(74) *Attorney, Agent, or Firm* — David L Pflugh

(57) ABSTRACT

The present invention relates to a hybrid vaccine for protecting a feline against diseases associated with respiratory diseases. The vaccine commonly includes a feline antigen. Methods for protecting felines against diseases associated with feline gastrointestinal and respiratory diseases, including but not limited to feline calicivirus, feline rhinotracheitis and feline panleukopenia, and methods of producing the feline vaccine are also provided.

14 Claims, No Drawings

(56) References Cited

OTHER PUBLICATIONS

Harris, E. L., & Angal, S. (1989). *Protein purification methods*. IRL Press at Oxford University Press.

Sambrook, J., Fritsch, E. F., & Maniatis, T. (1989). *Molecular cloning: a laboratory manual* (No. Ed. 2). Cold spring harbor laboratory press.

Bergmann, C., Stohlmann, S. A., & McMillan, M. (1993). An endogenously synthesized decamer peptide efficiently primes cytotoxic T cells specific for the HIV-1 envelope glycoprotein. *European journal of immunology*, 23(11), 2777-2781.

Bergmann, C. C., Yao, Q., Ho, C. K., & Buckwold, S. L. (1996). Flanking residues alter antigenicity and immunogenicity of multi-unit CTL epitopes. *The Journal of Immunology*, 157(8), 3242-3249.

Geysen, H. M., Meloen, R. H., & Barteling, S. J. (1984). Use of peptide synthesis to probe viral antigens for epitopes to a resolution of a single amino acid. *Proceedings of the National Academy of Sciences*, 81(13), 3998-4002.

Geysen, H. M., Rodda, S. J., & Mason, T. J. (1986). A priori delineation of a peptide which mimics a discontinuous antigenic determinant. *Molecular immunology*, 23(7), 709-715.

Burroughs, J. N., & Brown, F. (1974). Physico-chemical evidence for the re-classification of the caliciviruses. *Journal of General Virology*, 22(2), 281-286.

Nielsen, H. S., Liu, G., Nielsen, J., Oleksiewicz, M. B., Bøtner, A., Storgaard, T., & Faaberg, K. S. (2003). Generation of an infectious clone of VR-2332, a highly virulent North American-type isolate of porcine reproductive and respiratory syndrome virus. *Journal of virology*, 77(6), 3702-3711.

Suhrbier, A. (1997). Multi-epitope DNA vaccines. *Immunology & Cell Biology*, 75(4), 402-408.

Kahn, D. E., & Gillespie, J. H. (1970). Feline viruses. X. Characterization of a newly-isolated picornavirus causing interstitial pneumonia and ulcerativo stomatitis in the domestic cat. *Cornell Veterinarian*, 60, 669-683.

Schorr-Evans, E. M., Poland, A., Johnson, W. E., & Pedersen, N. C. (2003). An epizootic of highly virulent feline calicivirus disease in a hospital setting in New England. *Journal of Feline Medicine & Surgery*, 5(4), 217-226.

Tohya, Y., Masuoka, K., Takahashi, E., & Mikami, T. (1991). Neutralizing epitopes of feline calicivirus. *Archives of virology*, 117(3-4), 173-181.

Povey, R. C., & Hale, C. J. (1974). Experimental infections with feline calicivlruses (picornaviruses) in specific-pathogen-free kittens. *Journal of comparative pathology*, 84(2), 245-256.

Wensman, Jonas Johansson, Ayman Samman, Anna Lindhe, Jean-Christophe Thibault, Louise Treiberg Berndtsson, and Margaret J. Hosie. "Ability of vaccine strain induced antibodies to neutralize field isolates of caliciviruses from Swedish cats." *Acta Veterinaria Scandinavica* 57, No. 1 (2015):86.

Poulet, H., D. Jas, C. Lemeter, C. Coupier, and S. Brunet, "Efficacy of a bivalent inactivated non-adjuvanted feline calicivirus vaccine: relation between in vitro cross-neutralization and heterologous protection in vivo." *Vaccine* 26, No. 29 (2008): 3647-3654.

Day, M. J., M. C. Horzinek, and R. D. Schultz. "WSAVA guidelines for the vaccination of dogs and cats," *Journal of Small Animal Practice* 51, No. 6 (2010): 338-356.

Purevax RCPCH FeLV, European Public Assessment Report(EPAR), EMEA/V/V/085, (2008) 1-3.

Pesavento, Patricia A., N. J. MacLachlan, L. Dillard-Telm, C. K. Grant, and K. F. Hurley. "Pathologic, immunohistochemical, and electron microscopic findings in naturally occurring virulent systemic feline calicivirus infection in cats." *Veterinary Pathology* 41, No. 3 (2004): 257-263.

Pesavento, Patricia A., Kyeong-Ok Chang, and John SL Parker. "Molecular virology of feline calicivirus." *Veterinary Clinics of North America: Small Animal Practice* 38, No. 4 (2008): 775-786.

\* cited by examiner

HYBRID CORE FELINE VACCINES

BACKGROUND OF THE INVENTION

Field of the Invention

The present invention relates to a multivalent feline vaccine, which is capable of reducing clinical signs of infection associated with Feline Viral Rhinotracheitis, Calicivirus, including but not limited to Virulent Systemic Feline Calicivirus, and Feline Panleukopenia.

Feline Viral Rhinotracheitis (FVR) is an infectious disease caused by feline herpes virus type-1. Clinical signs include upper respiratory disease signs, conjunctivitis, and purulent ocular discharge.

Feline Calicivirus (FCV) is spread between cats through direct contact or fomites. Symptoms are similar to rhinotracheitis but also include oral or nasal ulcers. Virulent systemic calicivirus is a strain of FCV that causes generalized systemic disease and can lead to death in 67% of affected animals. Clinical signs include pyrexia, depression, jaundice, and symptoms of multiple organ disease. FCV is highly contagious and is extremely difficult to eradicate from the environment. Most FCV monovalent or multivalent vaccines do not contain a Virulent Systemic Feline Calicivirus (VS FCV) fraction.

Feline Panleukopenia Virus (FPV) is the feline equivalent to canine parvovirus type 2. Many feline practitioners count this as the most devastating of the three viruses. Clinical signs include pyrexia, anorexia, vomiting, diarrhea leading to extreme dehydration, and sudden death.

FVR and FCV comprise almost ninety percent of all feline respiratory infections; the availability of effective vaccines to prevent these two diseases is of great significance.

Some veterinarians have blamed modified live calicivirus vaccines for outbreaks of upper respiratory disease and malaise in their patients.

Studies have linked the development of some sarcomas to injections, specifically called Feline Injection Site-Associated Sarcomas (FISS). These tumors have increased in prevalence following the introduction of potent, adjuvanted vaccines. Possibly 1 to 4 in 10,000 vaccinated cats will develop an FISS after vaccination. The American Association for Feline Practitioners has recommended considering non-adjuvanted vaccines to try to reduce local inflammation in an effort to decrease the prevalence of FISS. The present invention is a non-adjuvanted combination of modified live and killed isolates, while others only currently have only all MLV or all KV versions.

SUMMARY OF THE INVENTION

The solution to the above technical problem is achieved by the description and the embodiments characterized in the claims. Thus, the invention in its different aspects is implemented according to the claims.

The present invention provides immunogenic compositions, vaccines, and related methods that overcome deficiencies in the art. The compositions and methods provide treatment of diseases in felines associated with Feline Viral Rhinotracheitis (FVR), Feline Calicivirus (FCV), including virulent systemic calicivirus (VS FCV) and Feline panleukopenia (FPV).

The present invention provides a combination of inactivated (killed) (KV) and modified live (MLV) feline vaccines. In particular, the invention provides improved feline isolates that have been identified below, or any descendant or progeny of one of the aforementioned isolates. Further, the present invention is adjuvant-free.

This vaccine of the present invention is a combination of modified live and killed strains, while existing feline vaccines currently have only all MLV or all KV versions. There is some concern that the use of an MLV calicivirus vaccine causes outbreaks of upper respiratory disease in treated patients due to potential reversion to virulence. The present invention uses a killed fraction to address this concern.

Further, the present invention includes a virulent systemic FCV fraction which provides a wider calicivirus coverage instead of relying on cross-protection.

It is contemplated that the vaccine may comprise a carrier that is suitable for intradermal or intramuscular application. In some embodiments, the vaccine is in freeze-dried form. In specific embodiments, the vaccine comprises at least about $10^7$ virus particles.

The present invention provides immunogenic compositions, vaccines, and related methods that overcome deficiencies in the art. The present invention relates to multivalent immunogenic compositions which include inactivated and modified live, attenuated fractions.

Another aspect of the invention relates to a method for the preparation of a hybrid inactivated and live, attenuated vaccine for combating feline disease, comprising admixing an inactivated and live attenuated vaccine of the present with a pharmaceutically acceptable carrier.

Immunogenic compositions and vaccines of the invention comprise inactivated and modified live components. This multivalent vaccine does not include an adjuvant. The vaccine may also include other components, such as preservative(s), stabilizer(s) and antigens against other swine pathogens.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include pharmaceutical- or veterinary-acceptable carriers, diluents, isotonic agents, stabilizers, or adjuvants.

Methods of the invention may also comprise admixing a composition of the invention with a veterinarily acceptable carrier. Those of skill in the art will recognize that the choice of carrier will be determined by the delivery route, personal preference, and animal species among others.

Methods for the treatment or prophylaxis of infections caused by the feline of the present invention are also disclosed. The method comprises administering an effective amount of the immunogenic composition of the present invention to an animal, specifically a feline. The treatment or prophylaxis is selected from the group consisting of reducing signs of feline infections associated with FRV, FCV (including VS FCV) or FPV, reducing the severity of or incidence of clinical signs of such infection, reducing the mortality of animals from such infections, and combinations thereof.

Herein, suitable subjects and subjects in need to which compositions of the invention may be administered include animals in need of either prophylaxis or treatment for a viral, microbial, parasitic, protozoan, bacterial, or fungal associated infection, disease, or condition. Most preferably, an immune response is stimulated in felines.

The invention provides a method of reducing the incidence of or severity of one or more clinical signs associated with or caused by a feline infection, comprising the step of administering an immunogenic composition of the invention as provided herewith, such that the incidence of or the severity of a clinical sign of the feline infection is reduced by at least 10%, preferably at least 20%, even more preferred at least 30%, even more preferred at least 50%, even more preferred at least 70%, most preferred at least 100% relative to a subject that has not received the immunogenic composition as provided herewith. Such clinical signs for FVR include upper respiratory disease signs, conjunctivitis, and purulent ocular discharge. For FCV, clinical signs are similar to FVR but also include oral or nasal ulcers. For VS FCV, clinical signs include generalized systemic disease, death, pyrexia, depression, jaundice, and symptoms of multiple organ disease. Clinical signs associated with FPV include pyrexia, anorexia, vomiting, diarrhea leading to extreme dehydration, and sudden death.

Preferred routes of administration include subcutaneous injection, oral, intradermal injection, and intramuscular injection. Administration subcutaneously (SC), in one or two doses, is preferred. The skilled artisan will recognize that compositions of the invention may also be administered in one or two or more doses, as well as, by other routes of administration. For example, such other routes include intranasally, intradermal, intravenous, intravascular, intraarterial, intraperitnoeal, intrathecal, intratracheal, intracardial, intralobar, intralobular, intramedullar, intravaginal, intrarectal, or intrapulmonary. Depending on the desired duration and effectiveness of the treatment, the compositions according to the invention may be administered once or several times, also intermittently, for instance on a daily basis for several days, weeks or months and in different dosages.

The new vaccines of this invention are not restricted to any particular type or method of preparation. These vaccines are prepared by standard methods known in the art.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

The invention provides a non-adjuvanted multivalent feline vaccine, which is capable of reducing clinical signs associated with infection with Feline Viral Rhinotracheitis, Calicivirus, including but not limited to Virulent Systemic Feline Calicivirus, and Feline Panleukopenia. The compositions and methods of the present invention provide treatment of diseases in felines associated with Feline Viral Rhinotracheitis (FVR), Feline Calicivirus (FCV), including virulent systemic calicivirus (VS FCV) and Feline panleukopenia (FPV).

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

It is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

"Feline Viral Rhinotracheitis" or "FVR", used interchangeably in this application, refers to an infectious disease caused by feline herpesvirus. The FVR of the present invention may be a KV or a MLV. However, it is preferred that this isolate be MLV. The FVR of the present invention is described in U.S. Pat. No. 4,287,178 and U.S. Pat. No. 4,031,204, both hereby incorporated by reference herein. A suitable KV FVR is deposited at American Type Culture Collection (ATCC), 10801 University Boulevard, Manassas, Va. 20110-2209, United States of America, and assigned accession number VR 814. A suitable MLV FVR is deposited at American Type Culture Collection (ATCC), 10801 University Boulevard, Manassas, Va. 20110-2209, United States of America, on Dec. 9, 1982 and assigned accession number VR 815 and is the preferred FVR isolate of the present invention. Other suitable FVR isolates are described in U.S. Pat. No. 4,791,062, U.S. Pat. No. 5,374,424 and U.S. Pat. No. 6,1070,103, all hereby incorporated by reference.

"Calicivirus" or "Feline Calicivirus" or "FCV", all used interchangeably in this application, refers to a single-stranded RNA virus capable of mutating into new isolates (See, J N Burroughs et al, "Physio-chemical evidence for the re-classification of the caliciviruses", J. Gen. Virol. 22: 281-286 (1974)) including but not limited to FCV-255, FCV-2280 (described in U.S. Pat. No. 4,522,810 and U.S. Pat. No. 6,231,863, hereby incorporated by reference and was deposited at the American Type Culture Collection (ATCC), 10801 University Boulevard, Manassas, Va. 20110-2209, United States of America, on Dec. 9, 1982 and assigned accession number VR-2057)), FCV-U1 (described in U.S. Pat. No. 6,355,246, hereby incorporated by reference), FCV-Diva (described in WO 2005/080416, hereby incorporated by reference), FCV-Kaos (described in U.S. Pat. Nos. 7,264,816 and 7,309,495, both hereby incorporated by reference), FCV-Bellingham, FCV-F9 (described in U.S. Pat. No. 3,944,469, hereby incorporated by reference), FCV-F4, FCV-M8 and FCV-DD1 (described in U.S. Pat. No. 8,685,412 and U.S. Pat. No. 8,685,42, both hereby incorporated by reference). There are non-hemorrhagic and hemorrhagic feline caliciviruses (also known as Virulent Systemic Feline Calicivirus). Preferably, the present invention encompasses both hemorrhagic and non-hemorrhagic feline caliciviruses (e.g., FCV and VS FCV). More specifically, the vaccine will comprise FCV-DD1, FCV-255, FCV-2280, and combinations thereof. More preferably, the vaccine will contain a mixture of FCV-DD1 and FCV-255. Preferably, the FCV's of the present invention are inactivated or killed, and preferably inactivated using formalin (see inactivated discussion below).

"Virulent Systemic Feline Calicivirus" or "VS FCV", used interchangeably in this application, refers to hemorrhagic feline caliciviruses and is an atypical, unusually virulent and highly contagious form of feline calicivirus (FCV) that results in a hemorrhagic fever syndrome in cats. FCV-DD1, FCV-Kaos, and FCV-Bellingham. FCV-Kaos was been deposited with the American Type Culture Collection (ATCC), 10801 University Boulevard, Manassas, Va. 20110-2209, United States of America, on Sep. 9, 2004, and has been assigned accession number PTA-5798. It is preferred that FCV-DD1 be used in the present invention. FCV-DD1 was deposited at the American Type Culture Collection (ATCC), 10801 University Boulevard, Manassas, Va. 20110-2209, United States of America, on Sep. 9, 2004, and has been assigned accession number PTA-6204.

"Feline Panleukopenia" or "FPV" or "FPL", used interchangeably in this application, refers to a virus caused by feline parvovirus. FPV is also known as feline infectious enteritis, feline parvoviral enteritis, feline ataxia, feline distemper or cat plague. The name panleukopenia is based on the low white blood cell count (leukocytes) exhibited by affected animals. Suitable FPV isolates of the present invention are described in U.S. Pat. No. 3,892,627, U.S. Pat. No. 5,374,424 and WO 93/01284, all incorporated by reference herein. The preferred FPV of the present invention is an MLV. The preferred isolate was isolated at Northmead Laboratories in 1967 from a feline kidney (FK) cell culture of an apparently normal kitten. It was attenuated by serial passage in feline embryo (KE10 and FK cell lines). The $51^{st}$ passage virus stock was imported from Arthur Webster Pty Limited, Australia and was passed once in the Crandell Feline Kidney (CRFK) cell line.

An "immunogenic or immunological composition or vaccine", all used interchangeably in this application, refers to a composition of matter that comprises at least one antigen of the present invention, or immunogenic portion thereof, that elicits an immunological response in the host of a cellular or antibody-mediated immune response to the composition. In a preferred embodiment of the present invention, an immunogenic composition induces an immune response and, more preferably, confers protective immunity against one or more of the clinical signs of a feline infection.

An "immunogenic" or "antigen" as used herein refer to a polypeptide or protein that elicits an immunological response as described herein. This includes cellular and/or humoral immune responses. Depending on the intended function of the composition, one or more antigens may be included be included. An "immunogenic" feline protein or polypeptide includes the full-length sequence of any of the feline antigens identified herein or analogs or immunogenic fragments thereof. The term "immunogenic fragment" or "immunogenic portion", used interchangeably in the application, refers to a fragment or truncated and/or substituted form of an antigen that includes one or more epitopes and thus elicits the immunological response described herein. In general, such truncated and/or substituted forms, or fragments will comprise at least six contiguous amino acids from the full-length protein. More preferably, the truncated or substituted forms, or fragments will have at least 10, more preferably at least 15, and still more preferably at least 19 contiguous amino acids from the full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. The term "vaccine" as understood herein is a modified live, attenuated vaccine for veterinary use comprising antigenic substances and is administered for the purpose of inducing a specific and active immunity against a disease provoked by a feline infection. The inactivated or attenuated feline vaccine, in particular the inactivated or modified live, attenuated feline vaccine as described herein, confer active immunity that may be transferred passively via maternal antibodies against the immunogens it contains and sometimes also against antigenically related organisms.

As used herein the terms "inactivated" or "killed" are used synonymously. Various physical and chemical methods of inactivation are known in the art. The term "inactivated" refers to a previously virulent or non-virulent virus or bacterium that has been irradiated (ultraviolet (UV), X-ray, electron beam or gamma radiation), heated, or chemically treated to inactivate, or kill, while retaining its immunogenicity. In one embodiment, the inactivated virus disclosed herein is inactivated by treatment with an inactivating agent. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus or bacterium. It is critical to adjust the amount of formalin to ensure that the material is inactivated but not so much that side effects from a high dosage occur.

Another suitable inactivation method is the use of ethylenimine and related derivatives, such as binary ethylenimine (BEI) and acetylethylenimine, are examples of suitable chemical inactivating agents for use in inactivating the virus. Other chemical inactivating agents, e.g., beta-propiolactone, aldehydes (such as formaldehyde) and/or detergents (e.g., TWEEN® detergent, TRITON® X, or alkyl trimethylammonium salts) can also be used to inactivate the virus. The inactivation can be performed using standard methods known to those of skill in the art. Samples can be taken at periodic time intervals and assayed for residual live virus. Monitoring of cytopathic effect on an appropriate cell line and/or fluorescent staining with an appropriate specific monoclonal or polyclonal antibody can be used to detect the presence of residual live virus.

Inactivation with BEI can be accomplished by combining a stock BEI solution (e.g., a solution formed by adding 0.1-0.2 M 2-bromo-ethylamine hydrobromide to 0.1-0.2 N aqueous NaOH) with viral fluids to a final concentration of about 1-5 mM BEI. Inactivation is commonly performed by holding the BEI-virus mixture at 35-40° C. (e.g., 37° C.) with constant mixing for 24-72 hours. Virus inactivation can be halted by the addition of sodium thiosulfate solution to a final concentration in excess of the BEI concentration (e.g., addition of sodium thiosulfate at 17% of the volume of BEI to neutralize excess BEI) followed by mixing.

More particularly, the term "inactivated" in the context of a virus means that the virus is incapable of replication in vivo or in vitro and, respectively, the term "inactivated" in the context of a virus means that the virus is incapable of reproduction in vivo or in vitro. For example, the term "inactivated" may refer to a virus that has been propagated in vitro, and has then been deactivated using chemical or physical means so that it is no longer capable of replicating. In another example, the term "inactivated" may refer to a virus that has been propagated, and then deactivated using chemical or physical means resulting in a suspension of the virus, fragments or components of the virus, such as resulting in a solution which may be used as a component of a vaccine.

The term "live vaccine" refers to a vaccine comprising a living, in particular, a living viral active component.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA)) and the mixture is subsequently lyophilized or dehydrated by other methods. Prior to vaccination, the mixture is then rehydrated in aqueous (e.g., saline, phosphate buffered saline (PBS)) or non-aqueous solutions (e.g., oil emulsion, aluminum-based adjuvant).

As used herein, "pharmaceutical- or veterinary-acceptable carrier" includes any and all solvents, dispersion media, coatings, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid (EDTA), among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention, an attenuated virus is one in which the virulence has been reduced so that it does not cause clinical signs of a feline infection but is capable of inducing an immune response in the target mammal, but may also mean that the clinical signs are reduced in incidence or severity in animals infected with the inactivated or attenuated feline in comparison with a "control group" of animals infected with non-attenuated, wild type feline virus and not receiving the inactivated or attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an inactivated, attenuated and/or avirulent feline isolate is one that suitable for incorporation into an immunogenic composition comprising inactivated and modified live components.

An "attenuated virus" is a viable ("live") virus, in which the virulence of the infectious agent has been reduced, e.g., though passaging the virus in a specific cell line, or through genetic manipulation of the viral genome. The attenuation of the virus pertains to its virulence (pathogenicity), but does not necessarily affect the replicative capability of a virus. An attenuated virus can still be capable of replication. Thus, it may be a strain of a virus whose pathogenicity has been reduced so that it will initiate the immune response without causing the specific disease. In the context of the present invention, an attenuated virus may be a feline whose pathogenicity has been abrogated or reduced by inactivating at least one gene or protein involved in virulence. In the present invention "attenuation" is synonymous with "avirulent". In this context, the term "reduce/reduced" means a reduction in pathogenicity of at least 10%, preferably 25%, even more preferably 50%, still more preferably 60%, even more preferably 70%, still more preferably 80%, even more preferably 90% and most preferably of 100% as compared to a control group.

"Modified live" means the virus has been reduced in virulence by any of several methods known in the art such, including but not limited to repeated passage in cell culture; forced adaptation to growth at normally-restrictive temperatures; treatment with chemical mutagens to force high numbers of mutations and selection for the desired characteristics; and deletion or insertion of genes using rDNA technology. By the term "non-virulent" or "avirulent" is meant the modified live virus exhibits reduced or no clinical signs of infection when administered.

"Virulent" refers to the ability of an isolate to cause disease associated with an infection. Virulence can be evaluated by observing disease progression in the animal. An example of a "virulent" strain of antigen or pathogen is that exemplified by the challenge strain, as described and used in the present invention.

"Avirulent" refers to isolates of viruses that are lacking in virulence. That is, avirulent strains, isolates, or constructs are non-pathogenic and are incapable of causing disease. As used herein the term "avirulent" is used synonymously with the term "non-virulent."

As used herein the terms "strain" or "isolate" are used interchangeably.

The term "wild type virus", as used herein, is in particular directed to an infectious pathogenic virus, which is particularly capable of causing feline infections.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to a titer measured in tissue culture infectious dose 50 or plaque forming units per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

The term "immunoreactive to virus" as used herein means that the peptide or fragment elicits the immunological response against viruses.

As used herein, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

Herein, "specifically immunoreactive" refers to an immunoreactive protein or polypeptide that recognizes an antigen characteristic of feline infection but does not react with an antigen characteristic of a strict challenge control.

"Protection against disease", "protective immunity", "functional immunity" and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of Feline Viral Rhinotracheitis (FVR), Feline Calicivirus (FCV), including virulent systemic calicivirus (VS FCV) and Feline panleukopenia (FPV).

Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent, preferably a feline generated FVR, FCV, VS FCV and/or FPV, respectively, in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

As used herein, the term "viremia" is particularly understood as a condition in which virus particles reproduce and circulate in the bloodstream of an animal, in particular of a cat.

The term "reduction of viremia" induced by virus means, but is not limited to, the reduction of virus entering the bloodstream of an animal, wherein the viremia level, i.e. the number of virus copies per mL of blood serum or the number of plaque forming colonies per deciliter of serum, is reduced in the serum of subjects receiving the composition of the present invention by at least 50% in comparison to subjects not receiving the composition and may become infected. More preferably, the viremia level is reduced in subjects receiving the composition of the present invention by at least 90%, preferably by at least 99.9%, more preferably by at least 99.99%, and even more preferably by at least 99.999%.

"Safety" refers to the absence of adverse consequences in a vaccinated animal following vaccination, including but not limited to: potential reversion of a bacterium-based or virus-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in the animal against a virus.

"Mortality", in the context of the present invention, refers to death caused by infection, and includes the situation where the infection is so severe that an animal is euthanized to prevent suffering and provide a humane ending to its life.

The present vaccines typically include inactivated and attenuated viruses formulated with a pharmaceutically acceptable carrier. The pharmaceutical forms suitable for injectable use commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabenes, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

The volume of a single dose of the vaccine of this invention may vary but will be generally within the ranges commonly employed in conventional vaccines. The volume of a single dose is preferably between about 0.1 ml and about 3 ml, preferably between about 0.2 ml and about 1.5 ml, more preferably between about 0.2 ml and about 0.5 ml at the concentrations noted above.

The vaccine compositions of the invention may be administered by any convenient means.

The subject to which the composition is administered is preferably a cat.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Preferred routes of administration include but are not limited to intranasal, oral, intradermal, and intramuscular. Administration intramuscularly or intravaginally, most preferably in a single dose, is desirable. The skilled artisan will recognize that compositions of the invention may also be administered in one, two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobarly, intralobally, intramedullarly, intrarectally, intravaginally or intrapulmonarily. Depending on the desired duration and effectiveness of the treatment, the compositions according to the invention may be administered once or several times, also intermittently, for instance on a daily basis for several days, weeks or months and in different dosages.

The compounds described herein can be administered to a subject at therapeutically effective doses to treat feline associated diseases. The dosage will depend upon the host receiving the vaccine as well as factors such as the size, weight, and age of the host.

Immunogenicity of a composition can be determined by monitoring the immune response of test subjects following immunization with the composition by use of any immunoassay known in the art. Generation of a humoral (antibody) response and/or cell-mediated immunity may be taken as an indication of an immune response. Test subjects may include animals such as pigs, mice, hamsters, dogs, cats, rabbits, cows, horses, sheep, and poultry (e.g. chickens, ducks, geese, and turkeys).

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., the bacterial levels (for example, by culturing of a sample from the subject), or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the composition can be tested in vitro for the desired therapeutic or prophylactic activity, prior to in vivo use in animals or humans. For example, in vitro assays that may be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art.

After vaccination of an animal to a feline vaccine or immunogenic composition using the methods and compositions of the present invention, any binding assay known in the art can be used to assess the binding between the resulting antibody and the particular molecule. These assays may also be performed to select antibodies that exhibit a higher affinity or specificity for the particular antigen.

In general, attenuation of virus may be generated from pathogenic virus isolates by repeated passaging in suitable host cells that are permissive to the virus until the virus shows the desired properties (WO 92/21375, WO 93/06211, WO93/03760, WO 93/07898, WO 96/36356, EP 0 676 467, EP 0 732 340, EP 0 835 930). Alternatively, it may be generated by genetic reengineering through use of an infectious clone, normally a full-length complementary DNA transcript of the viral genome (WO 98/18933, EP 1 018 557, WO 03/062407, Nielsen et al, J Virol 2003, 77:3702-371 1). Additionally, the virus may be passaged under non-native physiological conditions which include, but are not limited to, modified temperature, cells from non-host species or in the presence of mutagens.

The invention extends to feline strains which are derived from the strains through propagation or multiplication in an identical or divergent form, in particular descendants which possess the essential characteristics of the deposited strains. Upon continued propagation, the strains may acquire mutations most of which will not alter the properties of these strains significantly.

The isolates of the invention may also be further modified to impart further desirable properties to them. This may be achieved by classical propagation and selection techniques, like continued propagation in suitable host cells to extend the attenuated phenotype. Alternatively, the isolates may be genetically modified by directed mutation of the nucleic acid sequence of the genome of these strains by suitable genetic engineering techniques.

The feline strains of the present invention are suitable for vaccines of the invention can be grown and harvested by methods known in the art, e.g., by propagating in suitable host cells.

In particular, the vaccine, as mentioned herein, is a live vaccine and/or a modified live vaccine-attenuated vaccine. The strains of the feline according to the invention can be grown and harvested by methods known in the art, e.g. by propagating in suitable cells Modified live vaccines (MLV) are typically formulated to allow administration of $10^1$ to $10^7$ viral particles per dose, preferably $10^3$ to $10^6$ particles per dose, and more preferably $10^4$ to $10^6$ particles per dose (4.0-6.0 $\log_{10}$ TCID$_{50}$).

Antibodies, or binding portions thereof, resulting from the use of feline peptides of the present invention are useful for detecting in a sample the presence of viruses. This detection method comprises the steps of providing an isolated antibody or binding portion thereof raised against an feline peptide of the invention, adding to the isolated antibody or binding portion thereof a sample suspected of containing a quantity of virus and detecting the presence of a complex comprising the isolated antibody or binding portion thereof bound to the virus.

The antibodies or binding portions thereof of the present invention are also useful for detecting in a sample the presence of a peptide. This detection method comprises the steps of providing an isolated antibody or binding portion thereof raised against a peptide, adding to the isolated antibody or binding portion thereof a sample suspected of containing a quantity of the peptide, and detecting the presence of a complex comprising the isolated antibody or binding portion thereof bound to the peptide.

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby subjects may be tested for aberrant levels of the molecule to which the immunoglobulin binds, and/or for the presence of abnormal forms of such molecules. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In one aspect, an antibody of the invention that immunospecifically binds to a peptide may be used to diagnose, prognose or screen for a feline infection.

In another aspect, the invention provides a method of diagnosing or screening for the presence of a feline infection or immunity thereto, comprising measuring in a subject the level of immunospecific binding of an antibody to a sample derived from the subject, in which the antibody immunospecifically binds a peptide in which an increase in the level of said immunospecific binding, relative to the level of said immunospecific binding in an analogous sample from a subject not having the infectious disease agent, indicates the presence of feline.

Examples of suitable assays to detect the presence of feline peptides or antagonists thereof include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well-known in the art.

The binding activity of a given antibody may be determined according to well-known methods. Those skilled in the art will be able to determine operative and optimal assay conditions for each determination by employing routine experimentation.

An additional aspect of the present invention relates to diagnostic kits for the detection or measurement of virus. Kits for diagnostic use are provided, that comprise in one or more containers an anti-peptide antibody, and, optionally, a labeled binding partner to the antibody. Alternatively, the anti-peptide antibody can be labeled (with a detectable marker, e.g., a chemiluminescent, enzymatic, fluorescent, or radioactive moiety). Accordingly, the present invention provides a diagnostic kit comprising, an anti-feline peptide antibody and a control immunoglobulin. In a specific embodiment, one of the foregoing compounds of the container can be detectably labeled. A kit can optionally further comprise in a container a predetermined amount of a peptide recognized by the antibody of the kit, for use as a standard or control.

Yet another embodiment of the invention includes a kit for vaccinating a cat against diseases associated with felines comprising: a dispenser capable of administering a vaccine to a cat; and a vaccine of the present invention as described herein.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Comparative Serological Evaluation of Feline Panleukopenia Virus (FPV) Antibody Titers Between a Group Vaccinated with VS Code 16D7.20 and a Group Vaccinated with Feline Rhinotracheitis-Panleukopenia Vaccine, Modified Live Virus The objective of this study was to evaluate, by comparative serological assay, FPV antibody titers between a group vaccinated with Feline Rhinotracheitis-Calici-Panleukopenia Vaccine, Modified Live & Killed Virus (test group) and a group vaccinated with Feline Rhinotracheitis-Panleukopenia Vaccine, Modified Live Virus (reference group) for a lack of excessive interference. A lack of excessive interference was supported by the non-inferiority of test group FPV GMT relative to reference group FPV GMT post-vaccination.

The schedule of events for this study coincided with the schedule of events Schedule of Events

TABLE 1

Schedule of Events

| Study Day | Event |
|---|---|
| −1 | Collected blood sample |
| 0 | Group T01: Vaccinated with Product Control (PC) |
|  | Group T02: Vaccinated with Experimental Vaccine (EV) |
| 7 | Collected blood sample |
| 14 | Collected blood sample |
| 20 | Collected blood sample |
| 21 | Group T01: Vaccinated with PC |
|  | Group T02: Vaccinated with EV |
| 28 | Collected blood sample |
| 35 | Collected blood sample |
| 42 | Collected blood sample |

The Experimental Vaccine (EV) was a Feline Rhinotracheitis-Calici-Panleukopenia Vaccine, Modified Live & Killed Virus using FVR Strain PM, FPV Strain E and FCV Strains DD1 and 255. The two FCV fractions contained minimum immunizing doses of each fraction and the FVR and FPV fractions were at release titers. All four components were in a lyophilized form. On D0 and D21, just prior to vaccination, each vial of lyophilized product was reconstituted with 0.6 mL of sterile diluent.

The Product Control (PC) was Feline Rhinotracheitis-Panleukopenia Vaccine, Modified Live Virus. The PC was formulated containing FVR and FPV fractions at approximately the same titrations as in the EV and utilized the same bulk materials produced for the EV product. Both components were in a lyophilized form. On D0 and D21, just prior to vaccination, each vial of lyophilized product was reconstituted with 0.6 mL of sterile diluent. This was a blinded vaccination study conducted in the host animal. The study was a randomized complete or incomplete block design. The experimental unit was the individual feline.

Forty-four eligible felines were grouped into blocks of two within litter and assigned to treatment groups within blocks for Study 1. An additional 44 eligible felines were grouped into blocks of two within litter and assigned to treatment groups within blocks for Study 2. Each block contained one vaccinate and one control. Populations of both study studies were combined for FPV serology for this study. Felines for Study 1 were gang housed and commingled in Trailer 64, pens 1-6, or housed separately in pen 7 (Feline 126, PC group, D20 through D42). Felines for Study 2 were gang housed and commingled in Trailer 63, pens 1-6. Felines were fed a standard commercial diet with water and food available ad libitum.

Felines in Studies 1 and 2 were FPV seronegative (SN≤2) on D−1 and healthy by observation. No felines were removed from the study once the study was initiated.

Each animal in the EV group (Group T02) received a 0.5 mL dose of the EV SC in the dorsal scapular region on D0 and D21 via a sterile syringe and needle. Each animal in the PC group (Group 1) received a 0.5 mL dose of the PC SC in the dorsal scapular region on D0 and D21 via a sterile syringe and needle. Approximately 5 mL of whole blood was collected into a serum separator tube (SST) from each feline enrolled in each study on days −1, 7, 14, 20, 28, 25, and 42. Blood in SSTs was allowed to clot at room temperature. Blood samples from Studies 1 and 2 were spun down and serum was harvested, split and transferred to three appropriate tubes. At least 75% of felines in each treatment group must seroconvert to FPV (SN≥1:8) by D42 for the study to be valid. If less than 75% of felines per treatment group failed to seroconvert by D42, the study was invalid.

Host animal serological responses from the test group for the FPV component were evaluated for non-inferiority when compared to the reference group. The GMT response for the FPV component generated in the host animal group by vaccination with the EV was non-inferior to the GMT of the group vaccinated with the PC by no more than the equivalence margin. The equivalence margin was set at 63% (a 63% titer ratio corresponds to a difference of about two thirds of a two-fold dilution in a serial assay) of the FPV GMT of the EV group on either D35 or D42 compared the FPV GMT of the PC group on the corresponding study days.

Demonstration of lack of excessive interference by the killed Calicivirus fractions on the serological response to the FPV fraction of Feline Rhinotracheitis-Calici-Panleukopenia Vaccine, Modified Live & Killed Virus at either D35 or D42 supports a label claim of "aid in the prevention of disease due to Feline Panleukopenia Virus".

The non-inferiority of the antibody titers were assessed in a generalized linear mixed model with the log of the serum titers as the dependent variable and treatment, time and the treatment time interaction included as independent variables with repeated measures on day. Litter was included as a random effect.

The least squares means and 90% confidence intervals for the difference between the EV and PC vaccine groups at each time point were generated from the linear model. The confidence intervals were adjusted for multiple comparisons. The anti-log of the lower bounds adjusted for multiplicity provided the simultaneous lower 90% confidence limits on the ratio of the geometric mean serum titers of the EV group compared to the PC group. The equivalence margin was set at 63%.

Individual FPV serology results are presented in Section 16.3, Tables 10-11. All felines had a FPV SN titer of <2 on D−1 and all felines had a FPV SN titer >8 on D42.

Two weeks after the second vaccination, D35 least squares mean FPV SN titers were 90,175.67 and 81,208.64 for the EV and PC groups, respectively. A comparison of D35 90% lower confidence intervals for EV and PC groups demonstrated a ratio of 0.89. Three weeks after the second vaccination, D42 least squares mean FPV SN titers were 109,818.90 and 104,930.94 for the EV and PC groups, respectively. A comparison of D42 90% lower confidence intervals for the EV and PC group demonstrated a ratio of 0.80.

The objective of this study was to evaluate, by comparative serological assay, FPV antibody titers between a group vaccinated with Feline Rhinotracheitis-Calici-Panleukopenia Vaccine, Modified Live & Killed Virus (EV group) and a group vaccinated with Feline Rhinotracheitis-Panleukopenia Vaccine, Modified Live Virus (PC group) for a lack of excessive interference. The equivalence margin was set at 63% (a 63% titer ratio corresponds to a difference of about two thirds of a two-fold dilution in a serial assay) of the FPV GMT of the EV group on either D35 or D42 compared the FPV GMT of the PC group on the corresponding study days.

Days 35 and 42 were selected for analysis of the lack of interference of killed FCV antigens on the serological response to the FPV MLV fraction. Days 35 and 42 corresponded with 2 and 3 weeks post-booster vaccination, respectively. It was expected that maximum immune responses to killed antigens would be at these time points and if any interference were to occur to the MLV fractions, it would most likely be detected at these times. Other time points prior to D35 were not analyzed for this same reason.

Two weeks after the second vaccination, D35 least squares mean FPV SN titers were 90,175.67 and 81,208.64 for the EV and PC groups, respectively. A comparison of D35 90% lower confidence intervals for EV and PC groups demonstrated a ratio of 0.89. Three weeks after the second vaccination, D42 least squares mean FPV SN titers were 109,818.90 and 104,930.94 for the EV and PC groups, respectively. A comparison of D42 90% lower confidence intervals for the EV and PC groups demonstrated a ratio of 0.80.

A ratio of 0.89 on D35 and a ratio of 0.808 on D42 for FPV SN serology supports that two doses of killed FCV antigens did not cause excessive interference of the FPV MLV fraction of Feline Rhinotracheitis-Calici-Panleukopenia Vaccine, Modified Live & Killed Virus.

Example 2: Comparative Serological Evaluation of Feline Viral Rhinotracheitis (FVR) Antibody Titers Between a Group Vaccinated with the Vaccine of the Present Invention and a Group Vaccinated with Feline Rhinotracheitis-Panleukopenia Vaccine, Modified Live Virus The objective of this study was to evaluate, by comparative serological assay, Feline Viral Rhinotracheitis (FVR) antibody titers between a group vaccinated with Feline Rhinotracheitis-Calici-Panleukopenia Vaccine, Modified Live & Killed Virus (test group) and a group vaccinated with Feline Rhinotracheitis-Panleukopenia Vaccine, Modified Live Virus (reference group) for a lack of excessive interference.

The Schedule of Events is the same as described in Example 1. The Experimental Vaccine (EV) was Feline Rhinotracheitis-Calici-Panleukopenia Vaccine, Modified Live & Killed Virus with FVR Strain PM, FPV Strain E and FCV strains DD1 and 255. The two FCV fractions contained minimum immunizing doses of each fraction and the FVR and FPV fractions were at release titers. All four components were in a lyophilized form. On D0 and D21, just prior to vaccination, each vial of lyophilized product was reconstituted with approximately 0.6 mL of sterile diluent.

The Product Control (PC) was Feline Rhinotracheitis-Panleukopenia Vaccine, Modified Live Virus. The PC was formulated containing FVR and FPV fractions at approximately the same titrations as in the EV and utilized the same bulk materials produced in Table 3 for the EV product. Both components were in a lyophilized form. On D0 and D21, just prior to vaccination, each vial of lyophilized product was reconstituted with approximately 0.6 mL of sterile diluent.

Eighty-eight eligible felines were grouped into blocks of two and assigned to treatment groups as described in the study protocols for studies in Example 1. Each block contained one vaccinate and one control. The entire study population was utilized for serological evaluation as described for those studies. For the challenge studies in Example 1, the study population was randomly subdivided into two groups of at least 20 blocks each. Each group of at least 20 blocks was assigned to one of the two challenge studies, as outlined in the protocols for Studies in Example 1. Felines were housed as explained in Example 1 and must have been FVR seronegative (SN≤2) on Day −1 and healthy by observation.

On D0 and D21 just prior to vaccination, each vial of lyophilized product was reconstituted with 0.6 mL of sterile diluent. Each feline received a 0.5 mL dose of the EV or PC SC in the dorsal scapular region via a sterile syringe and needle on D0, and a booster vaccination of the same treatment and dose on D21.

Approximately 5 mL of whole blood was collected into a serum separator tube from each feline enrolled in studies 2013080 and 2013081 on days −1, 7, 14, 20, 28, 25, and 42. Blood in SSTs was allowed to clot at room temperature. Blood samples from Studies 2013080 and 2013081 were spun down and serum was harvested, split and transferred to three appropriate tubes by BIVI-R&D laboratory personnel. Each tube was labeled with the feline's ID number, study number (Study 2013080: one tube—2013080, one tube—2013082, and one tube—2013083; Study 2013081: one tube—2013081, one tube—2013082, and one tube—2013083), the date of collection, the study day and the sample type. Serum samples were held at −70±10° C. until tested.

A serum neutralization (SN) assay was used to measure the antibody titers to FPV for samples collected on days −1, 35 and 42. Briefly, serial two-fold dilutions of heat-inactivated sera delineated for this Study 3 were mixed with equal volumes of viral suspensions (100 to 300 TCID50). The serum-virus mixture was incubated at 35±2 degrees C. for 60±10 minutes, and then inoculated onto actively dividing Crandell Feline Kidney (CRFK) cells. The assay was performed in 96-well tissue culture plates. The plates were incubated in a humidified CO2 incubator (5±2% CO2) for 6±1 days. Plates were read by the detection of virus infection in CRFK cells by immunofluorescence using FPV-specific antibody conjugated to a fluorochrome. SN antibody titers (TCID50/mL) were calculated according to the Reed and Muench method.

At least 75% of felines in each treatment group must seroconvert to FVR (SN>1:2) by D42 for the test to be valid. If less than 75% of felines per treatment group failed to seroconvert by D42, the test was invalid.

Host animal serological responses from the test group for the FVR component were evaluated for non-inferiority when compared to the reference group. The geometric mean serological titer (GMT) response for the FVR component generated in the host animal group by vaccination with the EV must be non-inferior to the GMT of the group vaccinated with the PC by no more than the equivalence margin.

The equivalence margin was set at 63% (a 63% titer ratio corresponds to a difference of about two thirds of a two-fold dilution in a serial assay) of the FVR GMT of the EV group on either D35 or D42 compared the FVR GMT of the PC group on the corresponding study days.

Demonstration of lack of excessive interference by the killed Calicivirus fractions on the serological response to the FVR fraction of Feline Rhinotracheitis-Calici-Panleukopenia Vaccine, Modified Live & Killed Virus at either D35 or D42 supports a label claim of "aid in the prevention of disease due to Feline Viral Rhinotracheitis".

The non-inferiority of antibody titers were assessed in a generalized linear mixed model with the log of the serum titers as the dependent variable and treatment, time and the treatment time interaction included as independent variables with repeated measures on day. Litter was included as a random effect.

The least square means and their 90% confidence intervals for the difference between the EV and PC vaccine groups at each time point were generated from the linear model. The confidence intervals were adjusted for multiple comparisons. The anti-log of the lower bounds adjusted for multiplicity provided the simultaneous lower 90% confidence limits on the ratio of the geometric mean serum titers of the EV group compared to the PC group. The equivalence margin was set at 63%.

All felines were had a FVR SN titer of <2 on D-1, and all felines had a FVR SN titer >2 on Day 42.

Two weeks after the second vaccination, D35 least square mean FVR SN titers were 23.0847 and 19.3156 for the EV and PC groups, respectively. A comparison of D35 90% lower confidence intervals demonstrated a ratio of 0.94. Three weeks after the second vaccination, D42 least square mean FVR SN titers were 19.8826 and 16.2753 for the EV and PC groups, respectively. A comparison of D42 90% lower confidence intervals demonstrated a ratio of 0.91.

The objective of this study was to evaluate, by comparative serological assay, Feline Panleukopenia Virus (FPV) antibody titers between a group vaccinated with Feline Rhinotracheitis-Calici-Panleukopenia Vaccine, Modified Live & Killed Virus, VS Code 16D7.20 (EV group) and a group vaccinated with Feline Rhinotracheitis-Panleukopenia Vaccine, Modified Live Virus (PC group) for a lack of excessive interference.

All felines in each group seroconverted to FPV (SN>2) by D42, thus the criteria for a valid study were met.

Days 35 and 42 were selected for analysis of the lack of interference of killed FCV antigens on the serological response to the FVR MLV fraction. Days 35 and 42 corresponded with 2 and 3 weeks post-booster vaccination, respectively. It was expected that maximum immune responses to killed antigens would be at these time points and if any interference were to occur to MLV fractions, it be most likely be detected at these times. Other time points prior to D35 were not analyzed for this same reason.

Two weeks after the second vaccination, D35 least square mean FVR SN titers were 23.0847 and 19.3156 for the EV and PC groups, respectively. A comparison of D35 90% lower confidence intervals for EV and PC groups demonstrated a ratio of 0.94. Three weeks after the second vaccination, D42 least square mean FVR SN titers were 19.8826 and 16.2753 for the EV and PC groups, respectively. A comparison of D42 90% lower confidence intervals for the EV and PC groups demonstrated a ratio of 0.91.

A ratio of 0.94 on D35 and a ratio of 0.91 on D42 for FVR SN serology supports that two doses of killed FCV antigens did not cause excessive interference of the FVR MLV fraction of Feline Rhinotracheitis-Calici-Panleukopenia Vaccine, Modified Live & Killed Virus.

Example 3: Evaluation of Efficacy of the Feline Calicivirus Strain DD1 Fraction of Feline Rhinotracheitis-Calici-Panleukopenia Vaccine, Modified Live & Killed Virus The objective of this study was to evaluate the efficacy of the Feline Calicivirus (FCV) strain DD1 fraction (at minimum immunizing dose) of Feline Rhinotracheitis-Calici-Panleukopenia Vaccine, Modified Live & Killed Virus following challenge with virulent systemic FCV. Satisfactory completion of this study objective and demonstration of efficacy would support a label claim of prevention of disease due to virulent systemic Feline Calicivirus.

The criterion to achieve satisfactory efficacy and a label claim of prevention of disease due to virulent systemic Feline Calicivirus was that the Experimental Vaccine (EV) group must demonstrate a prevented fraction of ≥80% for FCV clinical disease compared with the Product Control (PC) group. In addition, the magnitude of oral/nasal shedding was analyzed between groups for supportive data and possibly an additional label claim.

The Schedule of Events for this study is presented in Table 2.

TABLE 2

Schedule of Animal Events

| Study Day | Event |
| --- | --- |
| Day −8 (D-8) | General health observations |
| D-7 | General health observations |
| D-6 | General health observations |
| D-1 | Health Examination; General health observations; Collected blood and oral/nasal swab samples |
| D0 | Group 1: Vaccinated with Product Control (PC) Group 2: Vaccinated with Experimental Vaccine (EV) |
| 1, 2, 3, 5, 7, 9, 12, 14, and 15 | General health observations |
| D7 | Collected blood sample |
| D14 | Collected blood sample |
| D20 | General heath observations; Collected blood sample |
| D21 | Group 1: Vaccinated with Product Control (PC) Group 2: Vaccinated with Experimental Vaccine (EV) |
| Days 19, 20, 22-24, 26, 28, 30, 33, 35, 37, 41, and 42 | General health observations |
| D28 | Collected blood sample |
| D35 | Collected blood sample |
| D42 | Collected blood sample |
| D46 | Collected rectal temperatures |
| D47 | Clinical observations and rectal temperatures |
| D48 | Clinical observations and rectal temperatures |
| D49 | Collected clinical observations, rectal temperatures, blood and oral/nasal swab samples; Challenged with VS FCV Strain DD1 |
| D50-D62 | Collected clinical observations, rectal temperatures and oral/nasal swab samples |
| D63 | Collected clinical observations, rectal temperatures, blood and oral/nasal swab samples; Euthanized |

The Experimental Vaccine (EV) in this study was Feline Rhinotracheitis-Calici-Panleukopenia Vaccine, Modified Live & Killed Virus containing FVR Strain PM, FPV Strain E, FCV Strains DD1 and 255. The EV was formulated where the two FCV fractions contained minimum immunizing doses of each fraction and the FVR and FPV fractions were at release titers. All four components were in a lyophilized form. On D0, just prior to vaccination, each vial of lyophilized product was reconstituted with 1.2 mL of sterile diluent. On D21, just prior to vaccination, each vial of lyophilized product was reconstituted with 0.6 mL of sterile diluent.

The Product Control (PC) was Feline Rhinotracheitis-Panleukopenia Vaccine, Modified Live Virus containing VR Strain PM and FPV Strain E. The PC formulation contained FVR and FPV fractions at approximately the same titrations as the EV product. On D0, just prior to vaccination, each vial of lyophilized product was reconstituted with 1.2 mL of sterile diluent. On D21, just prior to vaccination, each vial of lyophilized product was reconstituted with 0.6 mL of sterile diluent.

The challenge material (VS FCV) was strain DD1. On the day of challenge, a sufficient volume of challenge material was thawed and diluted with Minimum Essential Media (MEM) to a targeted dose of approximately $1 \times 10^{5.5-6.5}$ TCID50/mL. A sufficient amount of material was prepared for titration and the challenge procedure. On the day of challenge the diluted pre- and post-challenge material was titrated. Ten-fold serial dilutions of the challenge material were performed in MEM. Each dilution was added to 96 well plates containing CRFK cells. The plates were incubated at 35±2° C. for 3-5 days. Plates were observed for cytopathic effect characteristic of FCV infection. Titers (TCID50/mL) were calculated according to the Reed and Muench method. The challenge material had a mean titer of $1 \times 10^{5.7}$ TCID50/mL.

The experimental unit was the individual feline. Eighty-eight eligible felines were grouped into blocks of two within litter, when possible. Felines were randomly assigned to one of two treatment groups within a block (one-PC and one-EV). The study populations were randomly subdivided into two groups of at least 20 blocks each. Each group of at least 20 blocks was assigned to one of the two challenge studies, Studies 5 and 6.

Felines were gang housed and commingled in Building 132, isolation Rooms 6 and 8. There were 21 felines (EV=11, PC=10) in Room 6 and 22 felines (EV=11; PC=11) in Room 8 on D0. Each of these isolation rooms are animal biosafety level-2 (ABSL-2). Housing space was in compliance with applicable regulations of animal welfare.

Felines were fed a standard commercial diet with water and food available ad libitum. Felines requiring medical attention were treated as deemed necessary by a site veterinarian after consultation with the Study Monitor. Any animal that died during the course of the study or was moribund and euthanized was necropsied, and tissues were taken, as deemed necessary by a site veterinarian, to determine the cause of death.

Felines were FCV seronegative (SN≤2), negative for FCV from oral/nasal swabs, and healthy by observation for inclusion in this study.

Felines were in good health and nutritional status before initiation of the study as determined by a site veterinarian. Felines were sedated with an injection of ketamine and butorphanol IM just prior to each blood collection. A physical examination was conducted by a site veterinarian for each potential feline candidate on D-1. Only felines deemed healthy by physical examination were included in the study.

On D0 just prior to vaccination, each vial of EV or PC lyophilized product was reconstituted with 1.2 mL of sterile diluent. Each feline received a 0.6 mL dose of the EV or PC SC in the dorsal scapular region. Each feline was tranquilized/anesthetized on D49. Following collection of blood and oral/nasal swab samples, each feline received 0.25 mL per nare and 0.5 mL orally of challenge material.

Felines were observed once daily from D47 to D63 by the Study Investigator for clinical signs associated with VS FCV. Observations included:

Nasal discharge: 0=No discharge from either nostril; 1=Serous discharge noted from one or both nostrils; 2=Mucoid discharge noted from one or both nostrils; and 3=Mucopurulent discharge noted from one or both nostrils.

Ocular discharge: 0=No discharge from either eye; 1=Serous discharge noted from one or both eyes; 2=Mucoid discharge noted from one or both eyes; and 3=Mucopurulent discharge noted from one or both eyes.

Sneezing: 0=No sneezing noted during clinical observation; 1=Non-productive sneeze noted during clinical observation; and 2=Violent, productive sneezing bursts noted during clinical observation.

Oral Ulcers: 0=No ulcer present on the oral or external mucosa; 1=One or more ulcers <4 mm in size (small); and 2=One or more ulcers ≥4 mm in size (large).

Facial, Limb or Pinna Edema: 0=No facial, limb or pinna edema; 1=Mild edema, barely detectable by palpation of facial, limb or pinna areas; 2=Moderate edema—easily detectable by palpation of facial, limb or pinna areas, but not visible when feline is observed on exam table; and 3=Marked edema—visually present in facial, limb or pinna of the ear areas. Oyoderma or Alopecia: 0=No pyoderma or alopecia present; 1=Mild pyoderma or alopecia, single occurrence and <1 cm in diameter; 2=Moderate pyoderma or alopecia, single occurrence ≥1 cm in diameter or multiple sites <1 cm; and 3=Marked pyoderma or alopecia; multiple sites of ≥1 cm in diameter. Mortality—Death or Euthanasia: 0=No and 1=Yes Each animal in the EV group received a 0.5 mL dose of the EV SC in the dorsal scapular region on D21 via a sterile syringe and needle. Each animal in the PC group received a 0.5 mL dose of the PC SC in the dorsal scapular region on D21 via a sterile syringe and needle.

Rectal temperatures were taken once daily from D46 to D63 by the Study Investigator.

Approximately 5 mL of whole blood was collected from each feline into a serum separator tube on days −1, 7, 14, 20, 28, 35, 42, 49 and 63 by the Study Investigator.

Blood samples were spun down and serum was harvested, split and transferred to three appropriate tubes by BIVI-R&D laboratory personnel. Serum samples were held at −70±10° C. until tested.

A serum neutralization (SN) assay was used to measure the antibody titers to FCV from samples delineated for this study. Briefly, serial two-fold dilutions of heat-inactivated sera were mixed with equal volumes of viral suspensions (50 to 400 $TCID_{50}$). The serum-virus mixture was incubated at 35±2° C. for 60±10 minutes, and then inoculated onto cell monolayers of Crandell Feline Kidney (CRFK) cells. The assay was performed in 96-well tissue culture plates. The plates were incubated in a humidified $CO_2$ incubator (5±2% $CO_2$) for 4±1 days and observed for cytopathic effect characteristic of FCV infection. The SN antibody titers ($TCID_{50}$/mL) were calculated according to the Reed and Muench method.

Oral/nasal swab samples were collected on D-1 and from D49 to D63 by the Study Investigator or designees. A cotton-tipped swab was brushed against the mucosa of both nares, around the gums and under the tongue and placed into a tube. Each tube contained 2.0 mL of MEM containing 100 μg/mL of gentamycin. Tubes were labeled with the study number, animal ID number, the date of collection, study day and sample type.

Swabs/tubes were frozen at ≤−50° C. until samples were tested. Swabs/tubes were quickly thawed in a 36±1° C. water bath and then samples mixed by vortexing. Liquid was expressed from swabs, filtered through a 0.45 μm filter, and serially diluted in MEM containing 100 μg/mL of gentamycin. One tenth of mL of each dilution was overlaid onto a sub-confluent monolayer of CRFK cells grown in 96 well disposable microtiter plates. Plates were incubated at 36±1° C. for 3-4 days and observed for cytopathic effect characteristic of FCV infection. Titers ($TCID_{50}$/mL) were calculated according to the Reed and Muench method.

The criteria for a valid study were: All felines must be negative for FCV antibody (SN≤2) and oral/nasal swabs must be negative for FCV on D-1; All PC felines must remain FCV sero-negative (SN≤2) during the pre-challenge phase of the study; and Greater than or equal to 80% of PC felines must meet the positive clinical case definition for FCV infection.

To determine if efficacy to support a label claim of prevention of disease due to VS FCV was achieved, numbers of positive and negative VS FCV clinical cases were determined based on the following case definitions:

VS FCV Positive Clinical Case Definition was that a feline was listed as positive for VS FCV clinical disease if it demonstrated the following post-challenge:

Mortality: Feline died or was euthanized and necropsy findings were concurrent with VS FCV disease (hemorrhagic or consolidated lungs, subcutaneous edema); or no mortality and feline demonstrated at least one clinical sign listed below for two or more days with a rectal temperature ≥105.5° F. and at least one degree above baseline (D46 to D49); mild to marked facial, limb or pinna edema; mild to marked pyoderma or alopecia; or oral ulcers.

VS FCV Negative Clinical Case Definition: No mortality and feline demonstrated a clinical sign listed below for no more than one day with a rectal temperature ≥105.5° F. and at least one degree above baseline (D46 to D49); mild to marked facial, limb or pinna edema; mild to marked pyoderma or alopecia; or oral ulcers.

The amount of shedding of FCV for each feline was evaluated as a secondary outcome. The amount of FCV shedding was based upon daily TCID50/mL results obtained from oral/nasal swab samples. The criterion to achieve satisfactory efficacy and a label claim of prevention of disease due to VS FCV was that the EV group must demonstrate a prevented fraction of ≥80% for VS FCV clinical disease compared with the PC group.

Oral/nasal shedding was analyzed and the criterion to achieve a label claim of aid in the reduction of oral/nasal shedding was that there was a significant reduction in the daily mean TCID50/mL value for the EV group compared with the PC group ($p \leq 0.05$).

For the occurrence of clinical disease, the number of felines that met the criterion of clinical disease due to VS FCV were compared between treatment groups in a generalized linear mixed model with the occurrence of clinical disease (Yes=1 or No=0) as the binomial dependent variable and treatment included as an independent variable. The block variable (litter) was included as a random effect in the model. The analysis utilized the binomial distribution and log it link. The preventive fraction (adjusted for litter) was calculated based on the parameter estimates from this analysis.

For the evaluation of the amount of virus shedding, the daily amount of virus shed was compared between treatment groups in a generalized linear mixed model with the daily virus titer as the dependent variable and treatment, time and the treatment-time interaction included as independent variables with repeated measures on day. The block variable (litter) was included as a random effect in the model. The covariance structure utilized was the unstructured. Within day differences in least square means was estimated from the linear model.

Thirteen of twenty PC and one of twenty-one EV felines exhibited a daily rectal temperature >105.5° F. and at least one degree above baseline (mean rectal temperature from D46 to D49) for at least two days post-challenge. Fourteen of twenty PC and 0 of twenty-one EV felines exhibited facial, limb or pinna edema for at least two days post-challenge. Zero felines exhibited pyoderma/alopecia for at least two days post-challenge. Eight of twenty PC and 0 of twenty-one EV felines exhibited an oral ulcer for at least two days.

Four of twenty PC and zero of twenty-one EV felines exhibited mucoid or mucopurulent nasal discharge for at least one day post-challenge. Zero felines exhibited mucoid or mucopurulent ocular discharge for least one day post-challenge. Seven of twenty PC and zero of twenty-one EV felines exhibited violent, productive sneezing bursts for at least one day post-challenge.

Overall, 20 of 20 PC felines and 1 of 21 EV felines met the FCV clinical case definition as described above in Section 11.2. The estimated prevented fraction was 0.95 (95% Confidence Interval [CI] 0.76, 1.00).

Individual oral/nasal swab FCV titer data where the least squares mean of virus detected in PC oral/nasal swabs post-challenge ranged from 0.000 to ≥4.5 log 10 TCID50/mL. The least squares mean of virus detected in EV oral/nasal swabs post-challenge ranged from 0.000 to 4.2 log 10 TCID50/mL. The EV group shed significantly lower amounts of virus orally/nasally compared with the PC group on days 51, 52, and 54-61 (p≤0.0061). No differences were detected between groups for oral/nasal shedding of virus on D50, D53, D62 and D63 (p≥0.0662).

All felines were FCV sero-negative on D-1 and all PC felines remained FCV sero-negative through the day of challenge (D49). Experimental vaccine felines exhibited weak sero-conversion after the first vaccination and strong sero-conversion after the second vaccination. Fourteen days after challenge (D63), all remaining felines exhibited strong FCV sero-conversion.

The objective of this study was to evaluate the efficacy of the FCV strain DD1 fraction (at minimum immunizing dose) of Feline Rhinotracheitis-Calici-Panleukopenia Vaccine, Modified Live & Killed Virus, following challenge with VS FCV.

All felines were sero-negative for FCV antibody (SN≤2) and oral/nasal swabs were negative for FCV on D-1; all PC felines remained FCV sero-negative (SN≤2) during the pre-challenge phase of the study, and >80% of PC felines met the positive clinical case definition for VS FCV infection. These results highlight that criteria for a valid study were met.

Felines were vaccinated with essentially a half dose of PC or EV on D0 and full dose of PC or EV on D21; and were challenged with VS FCV strain DD1 on D49. The VS FCV positive clinical case definition was mortality or clinical symptoms (rectal temperature ≥105.5° F. and at least one degree above baseline, mild to marked facial, limb or pinna edema, mild to marked pyoderma or alopecia, or oral ulcers) for ≥2 days post-challenge. Three-PC felines and zero-EV felines were euthanized post-challenge for welfare reasons. Necropsy of these three-PC felines confirmed a diagnosis of VS-FCV. The remaining 17 PC felines met the clinical case definition of VS-FCV based on pyrexia, edema and/or oral ulcers for at least 2 days post-challenge. Conversely, only one of 21 EV felines met the clinical case definition for VS FCV clinical disease post-challenge. The estimated prevented fraction was 95.2% (95% Confidence Interval [CI] 76.2%, 99.9%).

Detection of virus in oral/nasal swabs was analyzed. Experimental vaccine felines had significantly less virus detected in oral/nasal swabs compared with PC felines on all post-challenge days except for study days 50, 53, 62 and 63. Peak detection of virus for the PC group occurred on D56 in which the PC group had a least squares mean of 3.289 log 10 TCID50/mL of virus detected in oral/nasal swabs. Conversely on D56, the EV had a least squares mean of 0.504 log 10 TCID50/mL of virus detected in oral/nasal swabs (p<0.0001). Oral/nasal swab data supports the efficacy of two doses of vaccine when felines were challenged with VS FCV. Duration of shedding could not be analyzed due to the fact that three PC felines and one EV feline were still shedding virus from oral/nasal secretions on D63, which precluded analyses for additional label claims.

As discussed above, all felines were FCV sero-negative on D-1 and all PC felines remained FCV sero-negative through the day of challenge (D49). Conversely, EV felines exhibited weak FCV sero-conversion after the first vaccination and strong FCV sero-conversion after the second vaccination.

These results support that Feline Rhinotracheitis-Calici-Panleukopenia Vaccine, Modified Live & Killed Virus, administered subcutaneously to healthy 8 week old susceptible kittens and boostered three weeks later protected kittens from VS FCV associated clinical disease and supports a label claim of aid in the prevention of disease caused by virulent systemic feline calicivirus.

Example 4: Evaluation of Efficacy of the Feline Calicivirus Strain 255 Fraction of Feline Rhinotracheitis-Calici-Panleukopenia Vaccine, Modified Live & Killed Virus The objective of this study was to evaluate the efficacy of the Feline Calicivirus (FCV) strain 255 fraction (at minimum immunizing dose) of Feline Rhinotracheitis-Calici-Panleukopenia Vaccine, Modified Live & Killed Virus, following challenge with virulent FCV. Satisfactory completion of this study objective and demonstration of efficacy would support a label claim of prevention of disease due to Feline Calicivirus. The criterion to achieve satisfactory efficacy and a label claim of prevention of disease due to Feline Calicivirus was that the Experimental Vaccine (EV) group must demonstrate a prevented fraction of ≥80% for FCV clinical disease compared with the Product Control (PC) group. In addition, the magnitude of oral/nasal shedding was analyzed between groups for supportive data. The Schedule of Events, experimental unit, randomization and housing were the same as in Example 3.

Felines were FCV sero-negative (SN≤2), negative for FCV from oral/nasal swabs, and healthy by observation for inclusion in this study. A physical examination was conducted by a site veterinarian for each potential feline candidate on D-1.

Only felines deemed healthy by physical examination were included in the study. On D0 just prior to vaccination, each vial of EV or PC lyophilized product was reconstituted with 1.2 mL of sterile diluent. Each feline received a 0.6 mL dose of the EV or PC SC in the dorsal scapular region. Each animal in the EV group received a 0.5 mL dose of the EV SC in the dorsal scapular region on D21 via a sterile syringe and needle. Each animal in the PC group received a 0.5 mL dose of the PC SC in the dorsal scapular region on D21 via a sterile syringe and needle.

Each feline was tranquilized/anesthetized on D49. Following collection of blood and oral/nasal swab samples, each feline received 0.25 mL per nare and 0.5 mL orally of challenge material. Felines were observed once daily by the Study Investigator from D47 to D63 for clinical signs associated with FCV. Clinical signs were evaluated under the same criteria as defined in Example 3.

Rectal temperatures were taken once daily from D46 to D63 by the Study Investigator. Approximately 5 mL of whole blood was collected from each feline into a serum separator tube on days −1, 7, 14, 20, 28, 35, 42, 49 and 63 by the Study Investigator.

A serum neutralization (SN) assay was used to measure the antibody titers to FCV from samples delineated for this study. Briefly, serial two-fold dilutions of heat-inactivated sera were mixed with equal volumes of viral suspensions (50 to 400 $TCID_{50}$). The serum-virus mixture was incubated at 35±2° C. for 60±10 minutes, and then inoculated onto cell monolayers of Crandell Feline Kidney (CRFK) cells. The assay was performed in 96-well tissue culture plates. The plates were incubated in a humidified $CO_2$ incubator (5±2% $CO_2$) for 4±1 days and observed for cytopathic effect characteristic of FCV infection. The SN antibody titers ($TCID_{50}$/mL) were calculated according to the Reed and Muench method.

Oral/nasal swab samples were collected on D-1 and from D49 to D63 by the Study Investigator or designees. A cotton-tipped swab was brushed against the mucosa of both nares, around the gums and under the tongue and placed into a tube. Each tube contained 2.0 mL of MEM containing 100 µg/mL of gentamycin. Tubes were labeled with the study number, animal ID number, the date of collection, study day and sample type.

Swabs/tubes were frozen at ≤−50° C. until samples were tested. Swabs/tubes were quickly thawed in a 36±1° C. water bath and then samples mixed by vortexing. Liquid was expressed from swabs, filtered through a 0.45 µm filter, and serially diluted in MEM containing 100 µg/mL of gentamycin. One tenth of a milliliter of each dilution was overlaid onto a sub-confluent monolayer of CRFK cells grown in 96 well disposable microtiter plates. Plates were incubated at 36±1° C. for 3-4 days and observed for cytopathic effect characteristic of FCV infection. Titers ($log_{10}$ $TCID_{50}$/mL) were calculated according to the Reed and Muench method.

The criteria for a valid study were that all felines must be negative for FCV antibody (SN≤2) and oral/nasal swabs must be negative for FCV on D-1; All PC felines must remain FCV sero-negative (SN≤2) during the pre-challenge phase of the study; and Greater than or equal to 80% of PC felines must meet the positive clinical case definition for FCV infection.

To determine if efficacy to support a label claim of prevention of disease due to Feline Calicivirus was achieved, numbers of positive and negative FCV clinical cases were determined based on the following case definitions:

FCV Positive Clinical Case Definition means that a feline exhibited at least one ulcer for two or more days, regardless of other upper respiratory infection clinical signs; if no ulcers were present and it exhibited one or more of the other clinical sign(s) listed below for ≥4 days, regardless of the presence of at least one ulcer, and including mucoid to mucopurulent nasal discharge, mucoid to mucopurulent ocular discharge, violent, productive sneezing bursts, and a daily rectal temperature ≥103.0° F. and at least one degree above baseline (mean rectal temperature from D46 to D49)

FCV Negative Clinical Case Definition means that no ulcer(s) or any other clinical signs were exhibited; no ulcers were present or one or more ulcer was present for <2 days and/or it exhibited one or more of the other clinical signs listed below for <4 days, and including.

The amount of shedding of FCV for each feline was evaluated as a secondary outcome. The amount of FCV shedding was based upon daily TCID50/mL results obtained from oral/nasal swab samples.

The criterion to achieve satisfactory efficacy and a label claim of prevention of disease due to FCV was that the EV group must demonstrate a prevented fraction of ≥80% for FCV clinical disease compared with the PC group and The criterion to achieve a reduction of oral/nasal shedding was a significant reduction in the daily mean $TCID_{50}$/mL value for the EV group compared with the PC group (p≤0.05).

Statistical methods are the same as described in Example 3.

No felines exhibited mucoid to mucopurulent ocular discharge, mucoid to mucopurulent nasal discharge, or violent, productive sneezing bursts, for at least four days post-challenge. Five of twenty-two PC and one of twenty-two EV felines exhibited a daily rectal temperature ≥103.0° F. and at least one degree above baseline (mean rectal temperature from D46 to D49) for at least four days post-challenge. Twenty of twenty-two PC and two of twenty-two EV felines, exhibited an ulcer for at least two days post-challenge.

Overall, 21 of 22 PC felines and 3 of 22 EV felines met the FCV clinical case definition. The estimated prevented fraction was 0.86 (95% Confidence Interval [CI] 0.54, 0.96).

The least squares mean of virus detected in PC oral/nasal swabs post-challenge ranged from 2.836 to 4.085 $log_{10}$ $TCID_{50}$/mL of FCV titer data. The least squares mean of virus detected in EV oral/nasal swabs post-challenge ranged from 2.285 to 3.111 $log_{10}$ $TCID_{50}$/mL. The EV group shed significantly lower amounts of virus orally/nasally compared with the PC group on days 50-61, and D63 (p≤0.0370). No difference was detected between groups for oral/nasal shedding of virus on D62 (p=0.0879).

All felines were FCV sero-negative on D-1 and all PC felines remained FCV sero-negative through the day of challenge (D49). Experimental vaccine felines exhibited weak sero-conversion after the first vaccination and strong sero-conversion after the second vaccination. Fourteen days after challenge (D63), all PC felines exhibited FCV sero-conversion; while all EV felines exhibited their highest level of FCV sero-conversion noted in the study.

The objective of this study was to evaluate the efficacy of the Feline Calicivirus (FCV) strain 255 fraction (at minimum immunizing dose) of Feline Rhinotracheitis-Calici-Panleukopenia Vaccine, Modified Live & Killed Virus, following challenge with virulent FCV.

All felines were sero-negative for FCV antibody (SN≤2) and oral/nasal swabs were negative for FCV on D-1; all PC felines remained FCV sero-negative (SN≤2) during the pre-challenge phase of the study; and >80% of PC felines met the positive clinical case definition for FCV infection. These results highlight that criteria for a valid study were met.

Felines were vaccinated with essentially a half dose of PC or EV on D0 and full dose of PC or EV on D21; and were challenged with FCV strain 255 on D49. Feline calicivirus infection is characterized by oral ulcers and upper respiratory symptoms. The FCV positive clinical case definition was at least one oral ulcer for two or more days (regardless of other upper respiratory clinical signs), or upper respiratory clinical signs (mucoid to mucopurulent nasal discharge, mucoid to mucopurulent ocular discharge, violent-productive sneezing bursts or a daily rectal temperature >103.0° F. and at least one degree above baseline) for ≥4 days post-challenge. No mortalities occurred post-challenge. Three of 22 EV felines and 21 of 22 PC felines met the clinical case definition for FCV clinical disease post-challenge. The FCV clinical case definition for both groups was mainly supported by the observation of oral ulcers for two or more days. Oral ulcers were noted for 2 or more days in 20 of 22 PC felines and 2 of 22 EV felines. One additional PC feline and one additional EV feline exhibited a daily rectal temperature >103.0° F. and at least one degree above baseline (mean rectal temperature from D46 to D49) for at least four days post-challenge. The estimated prevented fraction, based on the incidence of FCV clinical disease, was 0.86 (95% CI 0.54, 0.96).

Detection of virus in oral/nasal swabs was analyzed for possible additional label claims. Experimental vaccine felines had significantly less virus detected in oral/nasal swabs compared with PC felines on all post-challenge days except for D62. Although the EV group shed significantly less virus than PC felines, EV felines were still shedding moderate amounts of virus post-challenge. While statistical differences were detected between groups, these differences were not biologically significant.

No adverse events were associated with either vaccine during the post-vaccination and pre-challenge phase of the study. One EV feline exhibited failure to gain weight early in the study which was first noted before D0. Mild dehydration of felines in Room 410 for approximately half of a day was due to human error of inadvertently turning off the water to the room. The unformed stools in Room 409 and diarrhea in Room 410 could not be isolated to individual felines and were only noted for one day. Although a diagnosis for unformed stools and diarrhea was not determined, it was not likely due to booster vaccinations administered 2 weeks before the events.

As covered above, all felines were FCV sero-negative on D-1 and all PC felines remained FCV sero-negative through the day of challenge (D49). Conversely, EV felines exhibited weak FCV sero-conversion after the first vaccination and strong FCV sero-conversion after the second vaccination.

In conclusion, these results support that Feline Rhinotracheitis-Calici-Panleukopenia Vaccine, Modified Live & Killed Virus, VS Code 16D7.20 administered subcutaneously to healthy 8 week old susceptible felines and boostered three weeks later protected a significant number of felines from FCV associated clinical disease and supports a label claim of aid in the prevention of disease caused by feline calicivirus.

Example 5: Comparative Serological Evaluation of Feline Panleukopenia Virus (FPV) Antibody Titers Between a Group Vaccinated and a Group Vaccinated with Feline Rhinotracheitis-Panleukopenia Vaccine, Modified Live Virus The objective of this study was to evaluate, by comparative serological assay, Feline Panleukopenia Virus (FPV) antibody titers between a group vaccinated with Feline Rhinotracheitis-Calici-Panleukopenia Vaccine, Modified Live & Killed Virus (test group) and a group vaccinated with Feline Rhinotracheitis-Panleukopenia Vaccine, Modified Live Virus (reference group) for a lack of excessive interference. A lack of excessive interference was supported by the non-inferiority of test group FPV geometric mean titers (GMT) relative to reference group FPV GMT post-vaccination.

The Schedule of Events, EV, randomization, statistical analysis, animal care and housing are the same as in Example 1. The PC is a Feline Rhinotracheitis-Panleukopenia Vaccine, Modified Live Virus using FVR Strain PM and FPV Strain E. FVR and FPV fractions at approximately the same titrations as in the EV and will utilize the same bulk materials produced in Table 4 for the EV product. Both components were in a lyophilized form. On D0, just prior to vaccination, each vial of lyophilized product was reconstituted with 1.2 mL of sterile diluent. On D21, just prior to vaccination, each vial of lyophilized product was reconstituted with 0.5 mL of sterile diluent.

Felines were FPV sero-negative (SN≤2) and healthy by observation for inclusion in this study. On D0, just prior to vaccination, each vial of lyophilized product was reconstituted with 1.2 mL of sterile diluent. Each feline received a 0.6 mL dose of the EV or PC SC in the dorsal scapular region. This was a deviation from the protocol, which required the use of 0.5 mL of sterile diluent to reconstitute each treatment vial before administering 0.5 mL of respective treatment to each feline. The result of this deviation was that EV and PC felines received a half dose of vaccine antigens on D0.

Each animal in the EV group received a 0.5 mL dose of the EV SC in the dorsal scapular region on D21 via a sterile syringe and needle. Each animal in the PC group received a 0.5 mL dose of the PC SC in the dorsal scapular region on D21 via a sterile syringe and needle.

Approximately ≤5 mL of whole blood was collected into a serum separator tube (SST) from each feline enrolled in Studies 2013005 and 2013006 on days −1, 7, 14, 20, 28, 35 and 42. Blood in SSTs was allowed to clot at room temperature. Blood samples were spun down and serum was harvested, split and transferred to three appropriate tubes. A SN assay was used to measure the antibody titers to FPV. Briefly, serial two-fold dilutions of heat-inactivated sera delineated for this study were mixed with equal volumes of viral suspensions (100 to 300 TCID50). The serum-virus mixture was incubated at 35±2° C. for 60±10 minutes, and then inoculated onto actively dividing Crandell Feline Kidney (CRFK) cells. The assay was performed in 96-well tissue culture plates. The plates were incubated in a humidified CO2 incubator (5±2% $CO_2$) for 6±1 days. Plates were read for the detection of virus infection in CRFK cells by immunofluorescence using FPV-specific antibody conjugated to a fluorochrome. Serum neutralization antibody titers (TCID50/mL) were calculated according to the Reed and Muench method.

At least 75% of felines in each treatment group must seroconvert to FPV (SN≥1:8) by D42 for the study to be valid. If less than 75% of felines per treatment group failed to seroconvert by D42, the study was invalid.

Host animal serological responses from the test group for the FPV component were evaluated for non-inferiority when compared to the reference group. The GMT response for the FPV component generated in the host animal group by vaccination with the EV was non-inferior to the GMT of the group vaccinated with the PC by no more than the equivalence margin.

The equivalence margin was set at 63% (a 63% titer ratio corresponds to a difference of about two thirds of a two-fold dilution in a serial assay) of the FPV GMT of the EV group on either D35 or D42 compared the FPV GMT of the PC group on the corresponding study days.

All felines had a FPV SN titer <2 on D-1 and all felines remaining in the study on D42 had a FPV SN titer >8.

Two weeks after the second vaccination, D35 least squares mean FPV SN titers were 89,581.74 and 80,621.49 for the EV and PC groups, respectively. A comparison of D35 90% lower confidence intervals for the EV and PC groups demonstrated a ratio of 0.81. Three weeks after the second vaccination, D42 least squares mean FPV SN titers were 26,447.68 and 27,012.90 for the EV and PC groups, respectively. A comparison of D42 90% lower confidence intervals for the EV and PC group demonstrated a ratio of 0.68.

The objective of this study was to evaluate, by comparative serological assay, FPV antibody titers between a group vaccinated with Feline Rhinotracheitis-Calici-Panleukopenia Vaccine, Modified Live & Killed Virus, VS Code 16D7.20 (EV group) and a group vaccinated with Feline Rhinotracheitis-Panleukopenia Vaccine, Modified Live Virus (PC group) for a lack of excessive interference. The equivalence margin was set at 63% (a 63% titer ratio corresponds to a difference of about two thirds of a two-fold dilution in a serial assay) of the FPV GMT of the EV group on either D35 or D42 compared the FPV GMT of the PC group on the corresponding study days.

All felines remaining in the study sero-converted to FPV (SN≥8) by D42, thus the criterion for a valid study was met.

Days 35 and 42 were selected for analysis of the lack of interference of killed FCV antigens on the serological response to the FPV MLV fraction. Days 35 and 42 corresponded with 2 and 3 weeks post-booster vaccination, respectively. It was expected that maximum immune responses to killed antigens would be at these time points and if any interference were to occur to MLV fractions, it would most likely be detected at these times. Other time points prior to D35 were not analyzed for this same reason.

Two weeks after the second vaccination, D35 least squares mean FPV SN titers were 89,581.74 and 80,621.49 for the EV and PC groups, respectively. A comparison of D35 90% lower confidence intervals for EV and PC groups demonstrated a ratio of 0.81. Three weeks after the second vaccination, D42 least squares mean FPV SN titers were 26,447.68 and 27,012.90 for the EV and PC groups, respectively. A comparison of D42 90% lower confidence intervals for the EV and PC groups demonstrated a ratio of 0.68.

A ratio of 0.81 on D35 and a ratio of 0.68 on D42 for FPV SN serology supports that a half dose and a full booster dose of killed FCV antigens did not cause excessive interference of the FPV MLV fraction of Feline Rhinotracheitis-Calici-Panleukopenia Vaccine, Modified Live & Killed Virus.

Example 6: Comparative Serological Evaluation of Feline Viral Rhinotracheitis (FVR) Antibody Titers Between a Group Vaccinated and a Group Vaccinated with Feline Rhinotracheitis-Panleukopenia Vaccine, Modified Live Virus The objective of this study was to evaluate, by comparative serological assay, Feline Viral Rhinotracheitis (FVR) antibody titers between a group vaccinated with Feline Rhinotracheitis-Calici-Panleukopenia Vaccine, Modified Live & Killed Virus (test group) and a group vaccinated with Feline Rhinotracheitis-Panleukopenia Vaccine, Modified Live Virus (reference group) for a lack of excessive interference. A lack of excessive interference was supported by the non-inferiority of test group FPV geometric mean titers (GMT) relative to reference group FVR GMT post-vaccination.

The Schedule of Events, statistical analysis, randomization, animal health and welfare, EV and experimental unit are the same as in Example 1. The PC is a Feline Rhinotracheitis-Panleukopenia Vaccine, Modified Live Virus using FVR Strain PM and FPV Strain E. FVR and FPV fractions at approximately the same titrations as in the EV and utilized the same bulk materials produced in Table 2 for the EV product. Both components were in a lyophilized form. On D0, just prior to vaccination, each vial of lyophilized product was reconstituted with 1.2 mL of sterile diluent. On D21, just prior to vaccination, each vial of lyophilized product was reconstituted with 0.5 mL of sterile diluent.

Felines were FVR sero-negative (SN≤2) and healthy by observation for inclusion in this study.

On D0, just prior to vaccination, each vial of lyophilized product was reconstituted with 1.2 mL of sterile diluent. Each feline received a 0.6 mL dose of the EV or PC SC in the dorsal scapular region.

Approximately ≤5 mL of whole blood was collected into a serum separator tube from each feline enrolled in studies 2013005 and 2013006 on days −1, 7, 14, 20, 28, 35 and 42. Samples were collected by the Study Investigator.

Blood in SSTs was allowed to clot at room temperature. Blood samples from Studies 2013005 and 2013006 were spun down and serum was harvested, split and transferred to three appropriate tubes. Serum samples were held at −70±10° C. until tested.

A serum neutralization (SN) assay was used to measure the antibody titers to FVR. Briefly, serial two-fold dilutions of heat-inactivated sera were mixed with equal volumes of viral suspensions (50 to 400 $TCID_{50}$). The serum-virus mixture was incubated at 35±2° C. for 60±10 minutes, and then inoculated onto cell monolayers of Crandell Feline Kidney (CRFK) cells. The assay was performed in 96-well tissue culture plates. The plates were incubated in a humidified $CO_2$ incubator (5±2% $CO_2$) for 6±1 days and observed for cytopathic effect characteristic of FVR infection. The SN antibody titers ($TCID_{50}$/mL) were calculated according to the Reed and Muench method.

Each animal in the EV group received a 0.5 mL dose of the EV SC in the dorsal scapular region on D21 via a sterile syringe and needle. Each animal in the PC group received a 0.5 mL dose of the PC SC in the dorsal scapular region on D21 via a sterile syringe and needle.

At least 75% of felines in each treatment group must seroconvert to FVR (SN>1:2) by D42 for the test to be valid. If less than 75% of felines per treatment group failed to seroconvert by D42, the test was invalid.

Host animal serological responses from the test group for the FVR component were evaluated for non-inferiority when compared to the reference group. The geometric mean serological titer (GMT) response for the FVR component generated in the host animal group by vaccination with the EV must be non-inferior to the GMT of the group vaccinated with the PC by no more than the equivalence margin.

The equivalence margin was set at 63% (a 63% titer ratio corresponds to a difference of about two thirds of a two-fold dilution in a serial assay) of the FVR GMT of the EV group on either D35 or D42 compared the FVR GMT of the PC group on the corresponding study days.

All felines had a FVR SN titer of <2 on D-1, and 84 of 85 felines remaining in the study on D42 had a FVR SN titer >2. Two weeks after the second vaccination, D35 least square mean FVR SN titers were 6.2605 and 6.2750 for the EV and PC groups, respectively. A comparison of D35 90% lower confidence intervals demonstrated a ratio of 0.65. Three weeks after the second vaccination, D42 least square mean FVR SN titers were 11.1764 and 9.6755 for the EV and PC groups, respectively. A comparison of D42 90% lower confidence intervals demonstrated a ratio of 0.87.

The objective of this study was to evaluate, by comparative serological assay, Feline Viral Rhinotracheitis (FVR) antibody titers between a group vaccinated with Feline Rhinotracheitis-Calici-Panleukopenia Vaccine, Modified Live & Killed Virus (EV group) and a group vaccinated with Feline Rhinotracheitis-Panleukopenia Vaccine, Modified Live Virus (PC group) for a lack of excessive interference. Eighty-four of 85 (98.8%) remaining felines seroconverted to FVR (SN>2) by D42, thus the criteria for a valid study were met.

Days 35 and 42 were selected for analysis of the lack of interference of killed FCV antigens on the serological response to the FVR MLV fraction. Days 35 and 42 corresponded with 2 and 3 weeks post-booster vaccination, respectively. It was expected that maximum immune responses to killed antigens would be at these time points and if any interference were to occur to MLV fractions, it be most likely be detected at these times. Other time points prior to D35 were not analyzed for this same reason.

Two weeks after the second vaccination, D35 least square mean FVR SN titers were 6.2605 and 6.2750 for the EV and PC groups, respectively. A comparison of D35 90% lower confidence intervals for EV and PC groups demonstrated a ratio of 0.65. Three weeks after the second vaccination, D42 least square mean FVR SN titers were 11.11764 and 9.6755 for the EV and PC groups, respectively. A comparison of D42 90% lower confidence intervals for the EV and PC groups demonstrated a ratio of 0.88.

A ratio of 0.68 on D35 and a ratio of 0.88 on D42 for FVR SN serology supports that a half dose and a full booster dose of killed FCV antigens did not cause excessive interference of the FVR MLV fraction of Feline Rhinotracheitis-Calici-Panleukopenia Vaccine, Modified Live & Killed Virus.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

What is claimed is:

1. A non-adjuvanted immunogenic composition comprising:
   a. Feline Rhinotracheitis virus;
   b. Feline Calicivirus;
   c. Virulent Systemic Feline Calicivirus; and
   d. Feline Panleukopenia virus;
      wherein the Feline Calicivirus and the Virulent Systemic Feline Calicivirus are inactivated; and
      wherein the Feline Rhinotracheitis virus is attenuated.

2. The non-adjuvanted immunogenic composition according to claim 1, wherein the Feline Calicivirus and the Virulent Systemic Feline Calicivirus are physically inactivated by at least one treatment selected from the group consisting of UV radiation, X-ray radiation, gamma-radiation, freeze-thawing and heating, and any combination thereof.

3. The non-adjuvanted immunogenic composition according to claim 1, wherein the Feline Calicivirus and the Virulent Systemic Feline Calicivirus are chemically inactivated by treatment with at least one chemical inactivating agents selected from the group consisting of beta-propiolactone, gluteraldehyde, ethyleneimine, beta-ethyleneimine, binary ethyleneimine, acetylethyleneimine, ozone and formaldehyde, and any combination thereof.

4. The non-adjuvanted immunogenic composition according to claim 1, wherein the Feline Calicivirus is selected from the group consisting of: FCV-255, FCV-2280, FCV-U1, FCV-Diva, FCV-F9, FCV-F4, and FCV-M8.

5. The non-adjuvanted immunogenic composition according to claim 1, wherein the Virulent Systemic Calicivirus is selected from the group consisting of: FCV-DD1, FCV-Kaos, and FCV-Bellingham.

6. The non-adjuvanted immunogenic composition according to claim 4, wherein the Feline Calicivirus is FCV 255.

7. The non-adjuvanted immunogenic composition according to claim 5, wherein the Virulent Systemic Calicivirus is DD1.

8. The non-adjuvanted immunogenic composition according to claim 7, wherein the Feline Rhinotracheitis virus is selected from the group consisting of American Type Culture Collection (ATCC) accession number VR 814, and ATCC accession number VR 815, and a combination thereof.

9. The non-adjuvanted immunogenic composition according to claim 1, wherein the Feline Panleukopenia virus is attenuated.

10. The non-adjuvanted immunogenic composition according to claim 1, further comprising one or more pharmaceutically acceptable carriers and/or excipients.

11. A method for protecting a feline against diseases associated with Feline Rhinotracheitis virus, Feline Panleukopenia virus and Calicivirus, comprising administering to a feline in need thereof the immunogenic composition according to claim 1.

12. The non-adjuvanted immunogenic composition according to claim 10, wherein said non-adjuvanted immunogenic composition is in freeze-dried form.

13. A method of immunizing felines against diseases associated with Feline Rhinotracheitis virus, Feline Panleukopenia virus and Calicivirus, said method comprising the step of administering to felines the immunogenic composition according to claim 1.

14. The method according to claim 13, wherein a feline has reduced clinical signs or fails to exhibit clinical signs of diseases associated with Feline Rhinotracheitis virus, Feline Panleukopenia virus and Calicivirus subsequent to administration of the immunogenic composition according to claim 1.

* * * * *

UNITED STATES PATENT AND TRADEMARK OFFICE
CERTIFICATE OF CORRECTION

PATENT NO. : 10,188,725 B2
APPLICATION NO. : 15/375398
DATED : January 29, 2019
INVENTOR(S) : Jennifer Christine Hess et al.

Page 1 of 1

It is certified that error appears in the above-identified patent and that said Letters Patent is hereby corrected as shown below:

On the Title Page

Column 2 Line 4 item (56) (Other Publications): Delete "virus.Trials" and insert -- virus. Trials --, therefor.

In the Specification

Column 34 Line 27: In Claim 3, delete "gluteraldehyde," and insert -- glutaraldehyde --, therefor.

Signed and Sealed this
Nineteenth Day of March, 2019

Andrei Iancu
*Director of the United States Patent and Trademark Office*